United States Patent [19]

Granov et al.

[11] Patent Number: 5,236,410
[45] Date of Patent: Aug. 17, 1993

[54] TUMOR TREATMENT METHOD

[75] Inventors: Anatoli M. Granov; Vladimir Y. Derkach; Dmitry A. Granov, all of Leningrad, U.S.S.R.

[73] Assignee: Ferrotherm International, Inc., Denver, Colo.

[21] Appl. No.: 667,282

[22] Filed: Mar. 11, 1991

[30] Foreign Application Priority Data

Aug. 2, 1990 [SU] U.S.S.R. ............... 4848931

[51] Int. Cl.$^5$ ............... A61M 37/00
[52] U.S. Cl. ............... 600/12; 128/898; 128/899; 600/10
[58] Field of Search ............... 600/9-14; 128/898, 899, 399, 804; 424/9, 4

[56] References Cited

U.S. PATENT DOCUMENTS

| | | | |
|---|---|---|---|
| 4,545,368 | 10/1985 | Rand et al. | 600/12 |
| 4,574,782 | 3/1986 | Borelli et al. | 600/10 |
| 4,662,359 | 5/1987 | Gordon | 600/10 |
| 5,043,101 | 8/1991 | Gordon | 424/9 |
| 5,067,952 | 11/1991 | Gudov et al. | 600/10 |
| 5,108,359 | 4/1992 | Granov et al. | 600/9 |
| 5,120,527 | 6/1992 | Li et al. | 424/9 |

Primary Examiner—Lee S. Cohen
Assistant Examiner—Brian L. Casler
Attorney, Agent, or Firm—Phillips V. Bradford

[57] ABSTRACT

A method of treatment of a tumor comprising the steps of catheterization of the arterial vessel that feeds the tumor, and transcatheter administration of a suspension of magnetically hard ferromagnetic material in an oil solution of an oil-soluble antitumor substance with simultaneous application of local magnetic field onto the area of the tumor. After 1-3 days the tumor is subjected to ultrahigh radio frequency electromagnetic field or ultrasonic waves to produce heating of the tumor tissue to the temperature of 43.0°-43.5° C. for a period of 5-45 minutes.

32 Claims, No Drawings

TUMOR TREATMENT METHOD

FIELD OF THE ART

The invention relates to medicine, namely to tumor treatment methods, and may be used in oncology for the treatment of primary and metastatic tumors.

BACKGROUND OF THE INVENTION

At present the principal tumor treatment methods include surgical, chemotherapeutic, and radiation approaches. Surgical approach is efficient in cases of early diagnosis and smaller tumors without remote metastases. Large, advanced tumors may be removed only in rare cases, and this approach is often impossible.

The preferred method of conservative treatment of malignant tumors includes selective chemotherapy performed by injection of antitumor preparations into the blood vessels that supply the tumor, or directly into the tumor tissue or peritumoral region.

Known in the art is the method of treatment of malignant kidney tumors including chemoembolization of arterial network of the diseased kidney using an oil solution containing 100 mg of the anticancer substance Dioxadet, followed by occlusion of the main branch of the renal artery by a metal coil. Such chemoembolization leads to a reliable increase in the corrected indices of 3- and 5-year cumulative survival in patients with inoperable cancer of kidney parenchyma to $33.0\pm6.9\%$ and $24.5\pm6.75$ respectively, in comparison with the convenient embolization methods without a chemotherapeutic component, where these indices are $10.6\pm4.2\%$ and 0% (Anisimov V. A., et al. In: Modern Techniques in Roentgenosurgery, Abstr. IX Nat. Symp., Moscow, 1989, P. 118-119). However, gradually increasing intoxication caused by tumor decomposition sharply aggravates the patient's condition. Besides this, along with the tumor degradation products, tumor cellular elements are liberated into the venal bloodstream and lymphatic system, and may cause metastases.

Known in the art is a method of treatment of malignant liver tumors which includes embolization of the hepatic artery by a metal coil after the injection of Dioxadet (30-50 mg) dissolved in 6-9 ml of Myodil into its arterial branches (Granov A. M., Borisov A. E. In: "Endovascular Surgery of the Liver", Moscow, Meditsina, 1986, p. 137-138). Intraarterial infusion of chemotherapeutic agents provides better results as compared to intraportal infusion, since malignant tumors of the liver are supplied mainly by the arterial blood system. Therefore the intraarterial injection received wider application.

According to the inventors' data, remissions last up to 6-8 months, and one-year survival in patients with unresectable malignant tumors was 56.2%. The duration of remissions reported in the world medical literature for selective chemotherapy is 4-12 months. Anticancer substances are known to be toxic, especially when used systemically. The use of oil solutions somewhat reduces the general intoxication of the body due to retarded supply of a chemotherapeutic agent from an oil into tissues around the tumor. However, in spite of this fact, the decomposition of tumor tissue induced by chemotherapeutics, especially in bulky tumors, leads to sufficiently high intoxication and therefore worsens the general condition of a patient. Localization of an oil solution of chemotherapeutic agent in the tumor tissue for a period of 20-25 days often proves insufficient for the complete death of tumor cells. This disadvantage is further increased by the fact that oil solution eventually dissipates from the tumor. It brings about the need of repetitive intraorganous injections of a preparation and, as a consequence, yet more increase of intoxication.

Known in the art is also a method of treatment of hepatomas by chemoembolization using ferromagnetic particles followed by hyperthermia (Sako M., Hirota S. Gan To Kogaku Ryoho, 1986, vol. 13, No. 4, pt. 2, p. 1618-1624). Chemotherapeutic agent is administered into hepatic artery within the mixture containing a solution of carboxymethylcellulose or dextrane in a saline aqueous medium, and magnetically soft substance, metal iron, in the form of particles 30-50 mcm in size. The composition is confined within the tumor area by a local magnetic field. Hyperthermia is performed by induction heating of the magnetic particles. However, the large size of particles necessary for efficient induction heating (30-50 mcm) causes occlusion of the precapillary zone of the tumor. Therefore the prerequisites are created for preservation of viable parts of the tumor. Magnetically soft material may migrate out of the tumor area and dissipate in the course of tumor degradation. This phenomenon may lead to undesirable microembolizations. The use of water-based solutions of chemotherapeutic agents is known to provide a less pronounced prolongation effect because of the faster diffusion into tissues with consequent washing out of the organ. This process is increased by preserved organ blood flow. Beside this, the dissipation of ferromagnetic from the tumor area is inconvenient for monitoring of the tumor in remote periods and excludes the possibility of repeated hyperthermia procedures that may prove necessary. All said reasons increase probability of the tumor recurrence.

Known in the art is also the experimentally tested method of reduction of the tumor mass, based on the delivery into a tumor of magnetically hard ferromagnetic material using magnetic field, with consequent heating of the tumor at the expense of heat emitted by this ferromagnetic when placed into low-frequency oscillating electromagnetic field (U.S. Pat. No. 4,323,056). However, the said method employs heat treatment of a tumor alone, which, as evidenced by many reported data, is insufficient for complete necrosis and death of tumor cells.

Therefore, none of the known methods can provide complete necrosis of the tumor lesion without considerable intoxication and the risk of metastatic offspread.

SUMMARY OF THE INVENTION

It is therefore the main objective of the present invention to reduce the probability of recurrence of a tumor and of the offspread of metastases.

Another objective of the invention is to reduce systemic toxicity of the treatment.

The main and other objectives are achieved by the method for tumor treatment which involves first catheterization of the vessel that supplies a tumor of interest. Then, a suspension of a magnetically hard ferromagnetic substance in an oil solution of oil-soluble antitumor agent is injected through the catheter under fluoroscopic control and, at the same time, local magnetic field is applied onto the tumor-bearing area. After 1-3 days the tumor is subjected to oscillating power field selected from ultrahigh radio frequency electromagnetic field and the field of ultrasonic contraction waves until the temperature of 43.0°–43.5° C. is reached within the tumor, and this temperature is maintained for 5–45 minutes.

In cases of large size tumors it is preferable, according to the invention, to reduce the blood flow in the tumor-feeding blood vessel after the administration thereto of the said suspension.

The magnetically hard ferromagnetic substance preferably includes non-toxic non-corrosive iron containing material such as strontium hexaferrite ($SrO.6Fe_2O_3$) in the form of particles 0.5–7 mcm in size, which allow the ferromagnetic to penetrate also into capillary part of a tumor vasculature. This material is injected in the quantity of 1–9 grams suspended in 3–18 ml of the oil solution of an oil-soluble antitumor substance.

The oil solution of an antitumor agent may include the solution of alkylating aziridine derivative 2,4-bis-(1-aziridinyl)-6-(2.2-dimethyl-5-hydroxymethyl-1,3-dioxan-5-yl)amino-1,3,5-triazine known as Dioxadet (Granov A. M., Borisov A. E. In: "Endovascular Surgery of the Liver", Moscow, Medistina, 1986, P. 137–138) dissolved in an X-ray contrast oil preparation such as Myodil.

The radio-opaqueness of ferromagnetic material within the tumor allows to monitor the course of treatment by conventional X-ray examination.

According to the invention, the application of local magnetic field serves not only to confine the embolization within the tumor area, but also to form a compact, porous body of the ferromagnetic particles held together by magnetic forces, owing to the high residual magnetism of the hard ferromagnetic material. Such a compact magnetic system can withstand considerable hydrostatic pressure and provides reliable retention of the liquid phase of the embolizate within the tumor vasculature for a long time, without recanalization and dissipation of both ferromagnetic and liquid phase throughout the body. Therefore the antitumor agent is uniformly distributed within the tumor, while its systemic concentration is strongly reduced, and therapeutic index is improved. This advantage is further supported by the delivery of the antitumor agent in the form of an oil solution which is better retained within the embolizate due to its immiscibility with tissue and body fluids.

Thus, the stability of embolizate within the whole tumor-feeding vasculature in combination with prolonged chemotherapy and hyperthermia of a tumor reduces the proportion of viable tumor cells, prevents their migration outside the embolized area and therefore decreases the metastatic offspread. The antitumor agent, as well as the products of tumor tissue degradation, are prevented from migration outside the tumor focus; therefore toxic effects of the antitumor chemotherapeutic agent and of the tumor degradation products are substantially reduced.

DETAILED DESCRIPTION OF THE INVENTION

The method of the invention includes catherization of a blood vessel that supplies the tumor. This may be achieved by transcatheteral intraarterial injection of the tumor vasculature using an oil-based embolizing composition.

The composition contains an oil-soluble chemotherapeutic antitumor agent and provision of a ferrochemoembolizing composition consisting of a magnetically hard, radio-opaque ferromagnetic material suspended in an oil solution of an oil-soluble antitumor substance.

The magnetically hard ferromagnetic substance may be in the particulate form, which subsequently forms, within the injected embolizate, a stable porous network of magnetic particles held together by residual magnetism induced by the application of a constant magnetic field onto the tumor area.

This is achieved through the temporary application of an external constant magnetic field, such as produced by conventional samarium-cobalt permanent magnets.

This method of this invention includes the injection of the said ferrochemoembolizing composition through the said catheter, thus providing the formation, within the tumor vascular network, of a stable, compact, porous ferromagnetic aggregate harboring the said oil solution of the said oil-soluble antitumor substance. This stable porous network holds the embolizate and tissue degradation products within the focus of pathology for a long period, wherein the said ferromagnetic persists in the injected area.

In this manner, two aims are reached. First, the toxic components of the therapy are prevented from migration outside of the pathological focus, and the toxic side effects are reduced. Second, permanent embolization ceases the blood flow in the injection area and allows to enhance the degree of heating of the tumor during ultra-high RF or ultrasound hyperthermia of the tumor due to the lesser extent of heat dissipation in the embolized area in comparison with non-embolized normal tissues, and, due to the stability of embolizate, this phenomenon is observed long enough for the repetitive application of hyperthermia in remote periods after the treatment.

This method of this invention includes subsequent heating of the tumor by application of an oscillating power field to the tumor-bearing area, under the conditions that selectively produce necrosis of the tumor tissue Thus, the treatment of a tumor according to the invention includes certain steps that will now be described in further detail.

1. Catheterization of a Tumor Supply Vessel and Preliminary Investigation of a Tumor Vasculature This step is performed using conventional arterial catheterization and angiographic procedures. In case of liver tumors, the approach according to Seldinger is appropriate. The catheterization may be performed through a peripheral artery or intraoperationally, after the surgical isolation of a tumor-feeding vessel. The distribution patterns of radio-opaque ferromagnetic material released form a catheter are observed by fluoroscopy and provide information of the necessary quantity of embolizate, size of the tumor, etc. Finally, a catheter is placed in the distal part of the feeding artery in a closest position to the area to be ferrochemoembolized.

2. Preparing of the Ferrochemoembolizate

The ferrochemoembolizate to be supplied into tumor vasculature through a catheter consists of three components: Magnetically hard ferromagnetic substance in a powder form, oil medium, and an oil-soluble chemotherapeutic agent.

The ferromagnetic material to be used must be nontoxic after local injection, and show only negligible degradation when subjected to factors usually present in the human body. The ferromagnetic material must be in the form of particles with the size smaller than the lumen of the tumor capillaries, to ensure penetration of the ferrochemoembolizate into the tumor tissue, but large enough to provide necessary residual magnetization.

Success in one embodiment of this invention results wherein the said magnetically hard ferromagnetic material is non-toxic and non-degradable by tissue fluids, and, when transiently subjected to the said constant magnetic field, acquires residual magnetism sufficient to produce a compact mass that arrests the flow of water under the pressures up to 300 mm Hg, as measured in a cylindrical pipe, having the length-to-diameter ratio of the said compact mass equal to 3:1.

The ferromagnetic material must be magnetized when subjected to a magnetic field produced easily available sources suitable for manipulation, and acquire residual magnetism high enough to provide the formation of firm compact ferromagnetic mass which can resist the hydrostatic pressure usually present in the vascular system. The residual magnetism must be kept without significant decrease for a period sufficient for completion of the treatment course. Finally, the ferromagnetic should be preferably of low electrical conductivity to avoid its overheating in the ultrahigh RF electromagnetic field.

As demonstrated in the studies described below, hexaferrites of divalent metals, such as strontium and barium, meet the above requirements, and therefore have been used in the experimental and clinical embodiment of the present invention. Favorable results have been achieved wherein the said magnetically hard ferromagnetic material is selected from the group comprising barium hexaferrite and strontium hexaferrite. However, it should be noted that the variety of feromagnetics appropriate to the present method is not limited by this type of material.

In the first experiment, resistance of barium hexaferrite to dissolution was studied. The ferromagnetic material is in the form of particles 0.5–10 mcm in size. The powder of barium hexaferrite ($BaO.6Fe_2O_3$, particle size 0.5–10 mcm) was boiled in an acid solution (pH 2) for 1 hour. The proportion of the dissolved material was less than 2.5% of the initial quantity.

In the second experiment, stability of the magnetic moment acquired by barium hexaferrite after magnetization was studied. The ferromagnetic material (same as in the first experiment) was magnetized using a constant field with the field strength of 0.25 Tesla. The decrease of magnetic moment due to magnetic viscosity processes after one month were on the range of 1–3% of the initial value. Practically no changes in magnetic moment were observed after the effect of oscillating electromagnetic field with the amplitudes 100 times higher than the natural magnetic field of the Earth. Favorable results are achieved wherein the said magnetically hard ferromagnetic material, when magnetized and then subjected to oscillating electromagnetic field with the amplitude up to 100 times higher than that of the Earth, loses its acquired magnetic moment at a rate not more than 3% per month.

In the third experiment, the ability of magnetized suspension of barium hexaferrite to resist hydrostatic pressure was studied. For this purpose, suspension of barium hexaferrite (0.2 grams per 1 ml of physiological saline) was injected into a series of glass pipes with the inner diameters 0.33, 0.5, and 1.0 cm. The suspension was localized in the central part of the glass pipe by a permanent magnet with $B=0.2$ Tesla. After the model magnetic embol reached the length-to-diameter ration of 3:1, the magnet was removed, and hydrostatic pressure of a physiological solution was applied. No disruption of the magnetic embol was found for the pressures up to 300 mm of mercury. The filtration of a liquid began at the pressure of 500 mm of water, and stopped after 42 seconds due to the compaction of the ferromagnetic mass.

In the fourth experiment, the general and local toxicity of barium hexaferrite after its local injection in a tissue was studied. For this purpose, healthy white rats of both sexes were injected with suspension of barium hexaferrite described above in the dose of 0.05 g per 1 kg of body weight either subcutaneously or intramuscularly into the femoral area. The animals were followed during 14 days with the daily monitoring and during 12 months with monthly monitoring. No statistically reliable differences (Student-Fisher criterion) were found between the following parameters of injected and control animals: Blood hemoglobin, blood formula, total serum protein, urea and uric acid in the serum, liver enzymes and bilirubin, alkaline phosphatase, fibrinogen, clotting time, plasma recalcification time and plasma tolerance to heparin. No changes in the appearance, behavior of the animals, as well as in their progeny, were found. Histological examination of the tissue adjacent to the injected material demonstrated practically no short-time response. Minimal lymphocyte infiltration was observed in longer time (1 month) accompanied by the fragmentation of the injected ferrite mass by the newly formed connective tissue elements. No alteration of the muscle fibers was observed in the muscle tissue in the injection site, although the morphology of muscle tissue is known to be extremely sensitive to toxic factors. No morphological changes were found in the histology of liver, kidneys, spleen, lung, and brain of injected animals.

The ferromagnetic powder is divided into 1–2 gram portions and sterilized by autoclaving or gamma-radiation using conventional sterilizing protocols.

It is important that before injection the ferromagnetic component be demagnetized, wherein the said magnetically hard ferromagnetic material is demagnetized before use since the residual magnetism induced by the natural magnetic field of the Earth during storage of the ferromagnetic material may cause undesirable magnetic aggregation before the injection. The demagnetization can be performed by application of oscillating electromagnetic field of sufficient initial amplitude followed by gradual decrease of the field amplitude to zero. The devices and procedures for such process are well known in electronic engineering, e.g. in magnetic sound recording systems.

The ferromagnetic so prepared, typically in the quantity of 1–9 grams, is added to 3–18 ml of an oil solution containing oil-soluble antitumor agent, and mixed until homogenous suspension forms. The necessary volume of liquid component depends on the tumor size and vascularization, and is determined according to the results of angiography, as described above. Oils appropriate for this purpose may include mineral oils, various natural or processed oils of plant or animal origin, or radio-opaque oil-based pharmaceutic preparations used as X-ray contrasts, such as Iodolipol or Myodil. This invention may be practiced wherein the said oil is selected from the group comprising mineral oils, natural or processed oils of plant or animal origin, organosilicon oils, oil-based X-ray contrast pharmaceuticals, or combinations thereof, and specifically wherein the said oil is X-ray contrast oil-based pharmaceutical known as Myodil.

The oils most suitable for the described procedure are in principle the same as used for oil-based chemoembolization procedure earlier developed by the authors (Granov A. M., Petrovichev N. N. In: "Primary Cancer of the Liver", Leningrad, Meditsina, 1977, Chapter 6).

The choice of chemotherapeutic antitumor agnet is governed by its solubility in oils and efficiency against the particular tumor kind wherein the said oil-soluble antitumor substance is any chemical substance having the established antitumor activity, that can be dissolved in an oil in the concentration sufficient for cytotoxic effect in the tumor tissue adjacent to such solution. It may include alkylating agents, antibiotics, alkaloids, their hydrophobic derivatives, and other classes of antitumor agents, provided the above two criteria are met.

For the purpose of laboratory and clinical testing of the present invention, the particular alkylating anticancer agent was selected, having the chemical systematic name 2,4-bis-(1-aziridinyl)-6-(2,2-dimethyl-5-hydroxymethyl-1,3-dioxan-5-yl)amino-1,3,5-triazine, and trivial name Dioxadet. This compound proved efficient against various liver and kidney tumors when used in an oil solution in the form of chemoembolizate (see ref. above). Typically, 20–100 mg of Dioxadet are dissolved in 3–18 ml of an oil prior to the addition of the ferromagnetic component.

3. Ferrochemoembolization of the Vascular System of the Tumor

The ferrochemoembolization prepared as above is injected into a major tumor-feeding vessel through the catheter inserted according to Step 1. The volume of embolizate to be injected is chosen on the basis of angiographic data obtained during Step 1 and the size of the tumor, and may vary in the broad range from 1 to 50 ml or more. For the malignant tumors of liver and kidney, this volume was found to be usually within the range of 3–18 ml. The injection is performed in a slow and steady manner using a syringe of appropriate volume. During injection, local magnetic field is applied onto the tumor area. A permanent cylindrically shaped magnet producing a field of a sufficient field strength, preferably more than 0.2 Tesla, such as $SmCo_5$ magnet, may be used as the field source. In this embodiment of the invention, the said constant magnetic field has the field strength at least 0.2 Tesla. Several embodiments of this invention consist of steps wherein the constant magnetic field is applied 10 minutes after the injection of the ferrochemoembolizing composition and wherein the constant magnetic field is applied before, and at least 1 minute after the injection of the ferrochemoembolizing composition.

The diameter of the magnet is selected according to the size of the tumor focus. No fluoroscopic control of the procedure is performed during injection and application of the magnetic field because of the field-induced disturbances of the X-ray image. The injection usually takes 1–5 min. and the magnetic field is maintained for extra 5–10 minutes to ensure magnetization and magnetic aggregation of the ferromagnetic component within the injected composition.

Subsequently, the source of magnetic field is withdrawn, and the completeness of embolization is determined by fluoroscopy, owing to the high X-ray contrast of the ferromagnetic component. The fluorographs are taken for the further monitoring of tumor dynamics.

In case of larger tumors in highly vascularized parenchymal organs, such as liver, it is preferable that after the injection of the ferrochemoembolizate the blood flow in the tumor-feeding blood vessel is reduced. One procedure requires, after embolization, the arterial flow in the main tumor-feeding artery be reduced by insertion thereto of a metal Gianturco coil. This procedure is well understood by practitioners in endovascular surgery. An embodiment of this invention includes any practice wherein the reduction of the blood flow is produced by a metal coil inserted into the lumen of the artery through the same catheter.

After injection, the catheter is pulled somewhat back from the embolized area and left in the vessel for several days. At this time, it serves for the local and systemic administration of antibacterial, detoxifying and supportive therapy. Then the catheter may be withdrawn, or its distal opening may be sealed, inserted subcutaneously and left there until further treatment procedures will be necessary.

It is an embodiment of this invention wherein the systemic antibacterial, detoxification and supportive therapy is given after the injection of the ferrochemoembolizate, and systemic therapy is administered through the same catheter left in the same artery. This therapy consists of Cefsol (1 g×4 times daily); penicillin (6 units×6 times daily); up to 3 L saline solutions; and solutions containing 5–10% glucose, protease inhibitors, cardiotonics, vitamins, proteins and amino acids. In some cases said therapy is started at the first day after the injection of the ferrochemoembolizate, and said therapy is continued until no signs of intoxication are observed in a patient.

4. Hyperthermia of the Tumor

Heating of the embolized tumor focus is performed in order to ensure the necrosis of tumor and the death of tumor cells both by the effect of hyperthermia on the cell biochemistry and by the better availability of the liquid component-oil solution of an antitumor substance-to cancer cells within the tumor volume.

Among the known methods of hyperthermia used for the treatment of tumors, two methods of producing oscillating power fields have been selected as preferable for the purpose of the invention. One is radio frequency induced heating at the ultrahigh frequencies wherein the field frequency is 465 MHz., and the other oscillating power field is the field of ultrasonic expansion-compression waves propagating in an elastic medium. An example of the latter is ultrasonic hyperthermia produced by high frequency (1–2 MHz.) ultrasonic expansion-compression waves propagating through the liquid contact medium. In the first case, the technique may be practiced wherein said oscillating power field is a radio frequency electromagnetic field having a frequency higher than 100 mHz. In the second case, the technique may be practiced wherein the frequency of the said ultrasonic field is higher than 200 kHz. It is also possible that ultrasonic fields may be used wherein the frequency of the said field is between 1 and 2 MHz.

In both methods, the tumor is heated in such a manner that its temperature is raised to 42°–44° C., preferably to 43°–43.5° C., with a temperature differential of 3°–4° C. between the tumor and adjacent non-embolized tissue, and the above temperature is maintained for 5–45 min. The general protocol of heating is developed on the basis of previous laboratory and clinical investigations, and eventually allows to achieve complete aseptic necrosis of the embolized tumor with the subsequent shrinking and replacement of the necrotic mass by fibrous connective tissue. The exact protocol of heating is selected individually for each patient.

Selective heating of the tumor is ensured primarily by the absence of blood flow in the embolized tumor, while in adjacent normal tissue substantial proportion of heat is taken away by the bloodstream. The other important factor is that the RF field frequency and amplitude are chosen so as to produce efficient inductive heating of the tissue and only negligible heating of the ferromagnetic component. Therefore there is less danger of overheating and tissue burning.

The first hyperthermia session is conducted 1-3 days after the embolization. Histological examination of the changes that occur in tumor tissue after ferrochemoembolization shows that at that time the tumor capillaries are destroyed, and the oil solution of a chemotherapeutic agent starts to diffuse into intercellular spaces of the tumor tissue. Therefore the tumoricidal effect of the chemotherapeutic agent which releases slowly from the solution uniformly distributed within the tumor tissue. It allows to obtain pronounced destructive effect on the tumor cells within the heating time significantly smaller than that with vaso-occlusion alone (2-8 hours, of U.S. Pat. No. 4,708,718).

The use of ultrasonic heating is especially preferable for tumors of smaller size since this technique allows sharper focusing of the heat-generating oscillations in the small area with the characteristic linear size of 5 mm and less. Standard ultrasonic hyperthermia equipment or more advanced ultrasonic beam generators may be used for this purpose.

The hyperthermia procedure may be conducted one time or repetitively according to the progress of tumor necrosis as monitored by biopsies taken 6-7 days, 15-20 days, and 3-6 months after the embolization. Due to the stability of the ferrochemoembolizate and compaction of the necrotic mass, the repetitive hyperthermia does not require repetitive injections of the embolizing material.

The tumor dynamics following ferrochemoembolization according to the invention may be monitored by conventional X-ray examination of the tumor region, wherein the tumor is monitored by examination of the X-ray image produced by the said ferromagnetic material. Since the radio-opaque ferromagnetic component persists within the tumor focus and, as demonstrated by experimental and clinical observations described below, its X-ray image displays characteristic changes in accordance with the evolution of surrounding tumor tissue. Usually, shrinking oil the X-ray image of the ferromagnetic, its compaction and increase in density indicate successful destruction and replacement of the tumor tissue by a connective tissue.

The effect of the described ferrochemoembolizate on the tumor tissues was studied in rats with induced hepatic tumors. In the first experiment, hepatocellular cancer of the liver was induced in white laboratory rats (body weight 120-140 grams) by oral administration of a carcinogen diethylnitrosamine (DENA) as described elsewhere (Bykorez A. I., Pinchuk V. G. Experimental Tumors of the Liver, Naukova dumka, Kiev, 1976) Trial laparotomies were performed under appropriate anesthesia 4-9 months after the beginning of administration of the carcinogen.

The ferrochemoembolizing composition prepared as described in the Step 3 above was injected into hepatic artery of animals with pronounced primary tumor focuses in the liver without visible extrahepatic metastatic lesions. The injection was performed under visual control until the color of a tumor changed into dark brown, characteristic for the ferrochemoembolizate. During injection, a permanent magnet with H=0.1 Tesla was placed above the tumor. After 5 minutes, the magnet was removed, a temperature probe was fixed within the tumor tissue, and the abdominal wall was sutured in a conventional manner.

Then the tumor area was subjected to ultrahigh radio frequency electromagnetic field (UHRF apparatus "Ranet DMV-20-1", $P_{max}=15$ W, F=460 MHz, cylindrical probe o.d. 40 mm) for about 30 min. Temperature measurements indicated that during this procedure the temperature of the tumor raised to 42°-44° C., while in the adjacent tissues the temperature did not exceed 37°-39° C. It is an embodiment of this invention wherein the said heating raises the temperature of the ferrochemoembolized tumor to 42°-45° C., and wherein the said heating is applied so as to keep the temperature of the non-embolized tissue adjacent to the ferrochemoembolized tumor lower than 39° C. Our practice shows successful conclusions wherein the said heating is performed for a period between 5 and 60 minutes, and wherein the said heating is first performed within a period of 1-5 days after the ferrochemoembolization. The duration and starting time may fall within such ranges wherein the said heating is performed repetitively until the complete necrosis of the tumor cells is achieved.

Animals were sacrificed and subjected to pathological anatomic examination in the various periods. Histological examination of tumor tissue was performed using Van Gieson stain. In the first day, focuses of coagulation necrosis were found within the tumor. Vast structureless necrotic alterations in the tumor were observed on day 10, and on day 30 macrophage proliferation and substitution of fibrous connective tissue for the tumor tissue was observed within the tumor area. At this time, macroscopically, a fibrous lesion was determined in the liver in the place of the tumor, the injected ferromagnetic being preserved within the lesion. X-ray examination of the injected animals demonstrated that the pattern of the ferromagnetic observed after injection gradually contracted and became more compact. The treated animals displayed several times longer survival rates than untreated controls. In another experiment, white rats were inoculated into the liver edge by the cells of sarcoma-45. Animals with developed palpable tumors were treated as above, but, instead of RF electromagnetic field, ultrasonic waves with a frequency of 1 MHz were used for intraoperational hyperthermia, and the 15 mm gap between the sonicator probe and the tumor focus was filled with physiological saline solution. The temperature of 43°-43.5° C. was reached in the tumor focus within 10-12 sec., and maintained for 10 min. This experiment demonstrated the same results as the foregoing one.

The performance of the invention was further confirmed by clinical studies in patients having inoperable liver and kidney malignant tumors, as illustrated by the ongoing examples.

EXAMPLE 1

Male patient M., age 64. Diagnosis: recurrence of hepatocellular liver cancer, tubulotrabecular form In the anamnesis: Penetrating cut injure of the liver 34 years ago; dextral hemihepatectomy (V-VII segments) due to hepatocellular liver cancer. Primary tumor 12×10×10 cm. A single metastasis downstream of the blood vessels of adjacent liver tissue. Postoperational chemotherapy with Ftorafur through catheterized umbilical vein was performed twice with 6 month interval. 3 years ago regenerated right lobe of the liver was revised in the course of abdominal plastic surgery associated with postoperational ventral hernia: no evidence for cancer recurrence was observed. After two years: the patient complaints weakness, lost more than 5 kg of body weight, edema of low extremities. After examination, a recurrence of liver cancer within regenerated right lobe of the liver was diagnosed: tumor size 13×13 cm, deformation and obturation of lower vena cava in the region of the tumor. The patient was recognized inoperable.

The patient was treated according to the described method in the following manner. Under local potentiated anesthesia the hepatic artery of the patient was catheterized through femoral artery according to Seldinger. The character of tumor vascularization and the tumor localization were specified by angiography. Then the catheter was moved forward closer to the tumor area, and the suspension of 4 g of barium hexaferrite (particle size 0.5-7 mcm) in the solution of 20 mg of dioxadet in 6 ml of Myodil was injected through the catheter. In the course of injection and 10 minutes after injection a source of constant magnetic field was kept upon the projection zone of the tumor. In this embodiment of the invention the said constant magnetic field has the field strength of H=0.6 Tesla.

Then the catheter was retracted, and the Gianturco coil was inserted therethrough into the vessel. The catheter was left in the artery for 5 days, and through the catheter the supporting therapy including cephalosporine antibiotics, saline, polyion and protein solutions, diuretics, protease inhibitors, cardiotonics, diuretics and vitamins was performed. On day 6 the catheter was withdrawn, and systemic therapy was given until day 10. Hyperthermia of the tumor was first performed on day 2 by applying of RF field with the frequency of F=MHz for 45 min. During next 7 days the moderate fever (38° C.) was observed; pain syndrome was arrested by analgetics. Next examination after 6 months: the patient expresses no complaints, gained 6 kg weight, edema reduced. The patient is able to return to work. X-ray examination: contrast image of the tumor is more dense and reduced to 70-75% of its original size. Puncture biopsy: Coliquation necrosis with admixing ferromagnetic. Clinical and biochemical parameters of blood and urine within normal range. No metastases found. The patient is under observation.

EXAMPLE 2

Male patient S., age 60. Diagnosis: hepatocellular cancer of VI-VIII liver segments.

Ultrasonic examination revealed tumor focus 15 cm in diameter in VI-VIII liver segments, close to the dorsal surface of vena cava inferior, pushing the blood vessels aside. Puncture biopsy: hepatocellular cancer. Angiography: the tumor invaded both intrahepatic segmental branches of portal vein and the wall of vena cava inferior. The patient recognized inoperable.

The common hepatic artery of the patient was catheterized, and the catheter was moved into the artheria hepatica propria. Suspension of barium hexaferrite (6 g; particle size 0.5-7 mcm) in the solution of Dioxadet (30 mg) in Myodil (9 ml) was injected through the catheter into the tumor. During injection, a source of constant magnetic field similar to that of Example 1 was kept upon the skin projection of the tumor. In this embodiment of the invention the said constant magnetic field has the field strength of 0.6 Tesla.

Ten minutes after the injection the magnet was removed, and the localization of the formed compact ferromagnetic chemoembolyzing system in the tumor was confirmed by fluoroscopy. No adverse effects on the patient were observed during and after the roentgenendovascular administration of the ferrochemoembolizate.

On day 3 the patient was subjected to hyperthermia using the apparatus "Ranet DMV-20-1" (F=460 MHZ) for 30 min. Until day 9 after embolization the patient has moderate fever up to 38° C., felt weakness; until day 5-moderate pain syndrome. During first 5 days after embolization antibiotics (Cefsol 1 g×4 times daily; Penicillin 6 min units×6 times daily) were administered through the catheter left in the artery. At the same time, during the first 12 days after embolization the patient was given intravenously up to 3 L of saline solutions, 5-10% glucose, protease inhibitors, cardiotonics, vitamins, protein preparations and amino acid mixtures. X-ray examination performed on the day 6 demonstrated that the ferromagnetic was in the lumen of tumor vasculature. The Gianturco coil was inserted through the catheter into the common hepatic artery, and the catheter was withdrawn. Intravenous infusion therapy was continued until no signs of intoxication were detected. Puncture biopsy on day 20: necrosis and fibrosis around the aggregates and single particles of the ferromagnetic. The patient left hospital one month after embolization in fair condition with no signs of intoxication. Blood and urine parameters within the normal range for the patient's age. The patient is under observation more than 6 months.

EXAMPLE 3

Male patient S., age 55. Diagnosis: hypernephroid cancer of the left kidney.

Under the local potentiated anesthesia, the left renal artery was catheterized through the femoral artery. Angiography indicated no collaterals between the tumor vasculature and the blood vessels in the surrounding tissues. A source of constant magnetic field (H=0.6 Tesla) was mounted at the projection site of the tumor. The mixture of strontium hexaferrite (9 g) and the solution of Dioxadet (100 mg) in Myodil (18 ml) was injected into the tumor transcatheterally. 10 min. after the embolization the magnet was removed. Gianturco coil was inserted into the left renal artery through the catheter, and the catheter was withdrawn. X-ray examination confirmed the localization of ferrochemoembolizate within the tumor. On day 3 the patient was subjected to UHRF-hyperthermia using the apparatus "Ranet DMV-20-1", frequency 460 MHz, for 30 minutes. The patient tolerated the procedure of ferrochemoembolization fairly well. After the procedure, the subfebrile body temperature was observed for 4 days, and pain in the left lumbar area for 5 days. No hematuria was detected. The patient received intravenous infusion detoxification therapy as described in Example 2. On day 13 after embolization the biopsy was performed under the ultrasonic guidance. The biopsy material consisted of hypernephroid cancer tissue with massive necrotic areas and black ferrite granules. Second hyperthermia treatment was performed on the day 15 under the same conditions. The second hyperthermia procedure was painless to patient; transient increase in the body temperature to 37.5°-37.8° C. was observed. The patient left hospital on day 22 after the ferrochemoembolization in the fair condition, without complaints.

Since the patient categorically refused operation, no nephrectomy was performed.

Current examination after 6 months. The patient expresses no complaints, gained 4 kg weight. Puncture biopsy of the tumor region under the ultrasonic guidance: tumor tissue is represented by necrotic and fibrosis elements, without viable malignant cells. Clinical and biochemical parameters of blood and urine demonstrate that the tumor growth is arrested. The patient is under observation.

We claim:
1. A method of treatment of a tumor comprising:
   (a) catheterization of a blood vessel that supplies the tumor;
   (b) provision of a ferrochemoembolizing composition consisting of a magnetically hard, radio-opaque ferromagnetic material suspended in an oil solution of an oil-soluble antitumor substance;
   (c) application of a constant magnetic field onto a tumor area;
   (d) injection of said ferrochemoembolizing composition through said catheter, thus providing the formation, within the tumor vascular network, of a stable, compact, porous ferromagnetic aggregate harboring said oil solution of said oil-soluble antitumor substance; and,
   (e) subsequent heating of the tumor by application of an oscillating power field to the tumor-bearing area, under the conditions that selectively produce necrosis of the tumor tissue.

2. The method of claim 1, wherein said ferromagnetic material is in the form of particles 0.5-10 mcm in size.

3. The method of claim 2, wherein said magnetically hard ferromagnetic material is non-toxic and non-degradable by tissue fluids, and, when transiently subjected to said constant magnetic field, acquires residual magnetism sufficient to produce a compact mass that arrests the flow of water under the pressures up to 300 mm Hg, as measured in a cylindrical pipe, having the length-to-diameter ratio of said compact mass equal to 3:1.

4. The method of claim 3, wherein said magnetically hard ferromagnetic material is selected from the group consisting of barium-hexaferrite and strontium hexaferrite.

5. The method of claim 4, wherein said constant magnetic field has the field strength of at least 0.2 Tesla.

6. The method of claim 4, wherein said constant magnetic field has the field strength of 0.6 Tesla.

7. The method of claim 1, wherein said oil is selected from the group consisting of mineral oils, natural or processed oils of plant or animal origin, organosilicon oils, oil-based X-ray contrast pharmaceuticals, or combinations thereof.

8. The method of claim 7, wherein said oil is X-ray contrast oil-based pharmaceutical known as Myodil.

9. The method of claim 1, wherein said oil-soluble antitumor substance is any chemical substance having an established antitumor activity, that can be dissolved in an oil in a concentration sufficient for cytotoxic effect in the tumor tissue adjacent to such solution.

10. The method of claim 9, wherein said oil-soluble antitumor substance is 2,4-bis(1-azigidinyl)-6-(2,2-dimethyl-5-hydroxymethyl-1-1,3-dioxan-5-yl)amino-1,2,5-triazin, also known as Dioxadet.

11. The method of claim 1 wherein said ferromagnetic material is taken in the amount of 1-9 grams per 3-18 ml of said oil solution of the oil-soluble antitumor substance.

12. The method of claim 1, wherein said magnetically hard ferromagnetic material is demagnetized before use.

13. The method of claim 1, wherein the constant magnetic field is applied before, and at least 1 minute after the injection of the ferrochemoembolizing composition.

14. The method of claim 13, wherein the constant magnetic field is applied 10 minutes after the injection of the ferrochemoembolizing composition.

15. The method of claim 1, wherein after the injection of the ferrochemoembolizate the blood flow in the blood vessel that supplies the tumor is further reduced by another means.

16. The method of claim 15, wherein the reduction of the blood flow is produced by a metal coil inserted into the blood vessel that supplies the tumor through the same catheter.

17. The method of claim 1, wherein systemic antibacterial, detoxification and supportive therapy is given after the injection of the ferrochemoembolizate.

18. The method of claim 17, wherein the systemic therapy is administered through the catheter left in the blood vessel that supplies the tumor.

19. The method of claim 17, wherein said supportive therapy is started at the first day after the injection of the ferrochemoembolizate.

20. The method of claim 19, wherein said supportive therapy is continued until no signs of intoxication are observed in a patient.

21. The method of claim 1, wherein said oscillating power field is radio frequency electromagnetic field having a frequency higher than 100 MHz.

22. The method of claim 21, wherein the field frequency is 465 MHz.

23. The method of claim 1, wherein said oscillating power field is a field of ultrasonic expansion-compression waves propagating in an elastic medium.

24. The method of claim 23, wherein the frequency of said ultrasonic expansion-compression waves is higher than 200 KHz.

25. The method of claim 24, wherein the frequency of said expansion-compression waves is between 1 and 2 MHz.

26. The method of claim 1, wherein said heating raises the temperature of the ferrochemoembolized tumor to 42°-45° C.

27. The method of claim 26, wherein said heating is applied so as to keep the temperature of the non-embolized tissue adjacent to the ferrochemoembolized tumor lower than 39° C.

28. The method of claim 27, wherein said heating is performed for a period between 5 and 60 minutes.

29. The method of claim 28, wherein said heating is first performed within a period of 1-5 days after the ferrochemoembolization.

30. The method of claim 28, wherein said heating is performed repetitively until the complete necrosis of the tumor cells is achieved.

31. The method of claim 1, wherein said ferromagnetic material persists in the injected area.

32. The method of claim 31, wherein the tumor is monitored by examination of an X-ray image produced by said ferromagnetic material.

* * * * *